US009482682B2

(12) United States Patent
Ikeda et al.

(10) Patent No.: US 9,482,682 B2
(45) Date of Patent: Nov. 1, 2016

(54) REAGENT PREPARATION APPARATUS AND SAMPLE PROCESSING APPARATUS

(75) Inventors: Yutaka Ikeda, Kakogawa (JP);
Noriyuki Nakanishi, Kakogawa (JP)

(73) Assignee: SYSMEX CORPORATION, Hyogo (JP)

(*) Notice: Subject to any disclaimer, the term of this patent is extended or adjusted under 35 U.S.C. 154(b) by 273 days.

(21) Appl. No.: 13/417,886

(22) Filed: Mar. 12, 2012

(65) Prior Publication Data

US 2012/0237400 A1 Sep. 20, 2012

(30) Foreign Application Priority Data

Mar. 14, 2011 (JP) ................................. 2011-055629

(51) Int. Cl.
*G01N 35/00* (2006.01)
*G01N 27/00* (2006.01)
*G01N 33/50* (2006.01)
*G01N 1/38* (2006.01)

(52) U.S. Cl.
CPC .. *G01N 35/00663* (2013.01); *G01N 35/00613* (2013.01); *G01N 35/00712* (2013.01); *G01N 2035/00673* (2013.01); *Y10T 436/12* (2015.01); *Y10T 436/25* (2015.01)

(58) Field of Classification Search
None
See application file for complete search history.

(56) References Cited

U.S. PATENT DOCUMENTS

2010/0248289 A1    9/2010 Asahara et al.

FOREIGN PATENT DOCUMENTS

DK    WO 2009026919 A2 *    3/2009    ....... G01N 35/00029

* cited by examiner

*Primary Examiner* — Neil N Turk
(74) *Attorney, Agent, or Firm* — Brinks Gilson & Lione

(57) ABSTRACT

The present invention is a reagent preparation apparatus, comprising: a reagent preparation unit configured to prepare a reagent for processing a sample; a measuring unit configured to measure a property of the reagent prepared by the reagent preparation unit; a waste section configured to discard the prepared reagent when a measurement result by the measuring unit does not meet a predetermined condition; and a controller configured to control a reagent preparation operation of the reagent preparation unit, wherein the controller controls the reagent preparation unit to stop the reagent preparation operation when a number of times of discarding a reagent has reached a predetermined plurality of times.

14 Claims, 11 Drawing Sheets

FIG. 6

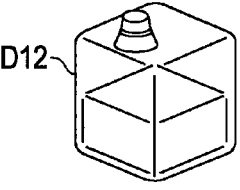

| THE REAGENT CAN BE SUPPLIED | ST | HELP |
| [CONDITION] | HC | |

⟨THE RESIDUAL AMOUNT OF HIGH CONCENTRATION REAGENT⟩

D12

LOT No. : 1234abcd
REPLACEMENT DATE : 2009/3/13
EXPIRATION DATE : 2009/5/13

⟨SERVICE PARTS INFORMATION⟩
FILTER : −
DIAPHRAGM PUMP 1 : −
DIAPHRAGM PUMP 2 : −
CONDUCTANCE METER : −

[SELECT] [REAGENT] [PREPARATION INTERRUPT] [SHUTDOWN]
  D13      D14         D15              D16

FIG. 7

THE REAGENT CAN BE SUPPLIED | ST | HELP
[PREPARATION HISTORY] | HC |

D22

| DATE | TIME | RESULT | TEMPERATURE | CONDUCTANCE |
|------|------|--------|-------------|-------------|
| 08/07/28 | 09:00 | OK | 25.0 | 13.25 |
| 08/07/28 | 09:01 | NG | 25.8 | 13.60 |
| 08/07/28 | 09:02 | WA | 24.5 | 13.45 |
| 08/07/28 | 09:03 | BD | 25.2 | 12.50 |

[RETURN]

REAGENT PREPARATION APPARATUS AND SAMPLE PROCESSING APPARATUS

RELATED APPLICATIONS

This application claims priority under 35 U.S.C. §119 to Japanese Patent Application No. 2011-055629 filed on Mar. 14, 2011, the entire content of which is hereby incorporated by reference.

FIELD OF THE INVENTION

The present invention relates to a reagent preparation apparatus capable of preparing reagent for use in sample processing, and a sample processing apparatus.

DESCRIPTION OF THE RELATED ART

For example, U.S. Patent Publication No. 2010/0248289 discloses a reagent preparation apparatus for preparing reagent for use in sample processing by mixing a predetermined amount of concentrated reagent and a predetermined amount of purified water in a mixing chamber. This reagent preparation apparatus is configured to measure a quality (electric conductivity) of the prepared reagent using a conductance meter, and transport the prepared reagent to a supply chamber when the conductance of the reagent falls within a predetermined range. On the other hand, this reagent preparation apparatus is also configured to discard the prepared reagent from a discard flow path when the conductance of the reagent is not within the predetermined range.

The present inventors discovered that the reagent quality (electrical conductivity) being outside the predetermined range is caused by persistent failure resulting from damage of hardware such as valves and pumps within the apparatus, and transient failure resulting from temporary changes of water quality of the purified water that is mixed with the concentrated reagent, and external static and the like.

In the case of persistent failure, the failure often cannot be resolved without repairing the hardware. Continuing the reagent preparation operation under such conditions is undesirable from the perspectives of the increase in the amount of wasted reagent, running cost and environmental burden. In the case of transient failure, however, it is preferable to continue the reagent preparation operation since the transient failure often may be resolved when the preparation operation is performed once or several times, and a reduction in operating efficiency of the apparatus can be prevented by reducing the downtime of the apparatus.

SUMMARY OF THE INVENTION

The scope of the present invention is defined solely by the appended claims, and is not affected to any degree by the statements within this summary.

A first aspect of the present invention is a reagent preparation apparatus, comprising: a reagent preparation unit configured to prepare a reagent for processing a sample; a measuring unit configured to measure a property of the reagent prepared by the reagent preparation unit; a waste section configured to discard the prepared reagent when a measurement result by the measuring unit does not meet a predetermined condition; and a controller configured to control a reagent preparation operation of the reagent preparation unit, wherein the controller controls the reagent preparation unit to stop the reagent preparation operation when a number of times of discarding a reagent has reached a predetermined plurality of times.

A second aspect of the present invention is a reagent preparation apparatus, comprising: a reagent preparation unit configured to prepare a reagent for processing a sample; a measuring unit configured to measure a property of the reagent prepared by the reagent preparation unit; a waste section configured to discard a prepared reagent when a measurement result by the measuring unit does not meet a predetermined condition; and a controller configured to control a reagent preparation operation of the reagent preparation unit, wherein the controller controls the reagent preparation unit to stop the reagent preparation operation when a number of times of a measurement result does not meet a predetermined condition has reached a predetermined plurality of times.

A third aspect of the present invention is a sample processing apparatus, comprising: a sample processing section configured to process a sample using a predetermined reagent; a reagent preparation unit configured to prepare the predetermined reagent; a measuring unit configured to measure a property of the reagent prepared by the reagent preparation unit; a waste section configured to discard the prepared reagent when the measurement result by the measuring unit does not meet a predetermined condition; and a controller configured to control a reagent preparation operation of the reagent preparation unit, wherein the controller is configured to control the reagent preparation unit to stop the reagent preparation operation when a number of times that the measurement result by the measuring unit does not meet the predetermined condition has reached a predetermined plurality of times.

BRIEF DESCRIPTION OF THE DRAWINGS

FIG. 6 is a screen view showing an example of a display screen that is displayed on the display/operating unit of the embodiment of the reagent preparation apparatus of the present invention;

FIG. 7 is a screen view illustrating the preparation history display screen displayed on the display/operating unit of the embodiment of the reagent preparation apparatus of the present invention;

DETAILED DESCRIPTION OF THE PREFERRED EMBODIMENTS

The preferred embodiments of the present invention will be described hereinafter with reference to the drawings.

The embodiment is described below by way of a blood analyzer for analyzing blood as an example of a sample analyzer based on the drawings.

The embodiment of the present invention is described below based on the drawings.

The structure of the sample processing apparatus 1, an embodiment of the present invention, is described below referring to FIGS. 1 through 5 and FIGS. 8 through 13. Note that, in this embodiment, the present invention is applied to a reagent preparation apparatus 4 of the sample processing apparatus 1, which performs blood analysis.

Figure 1:
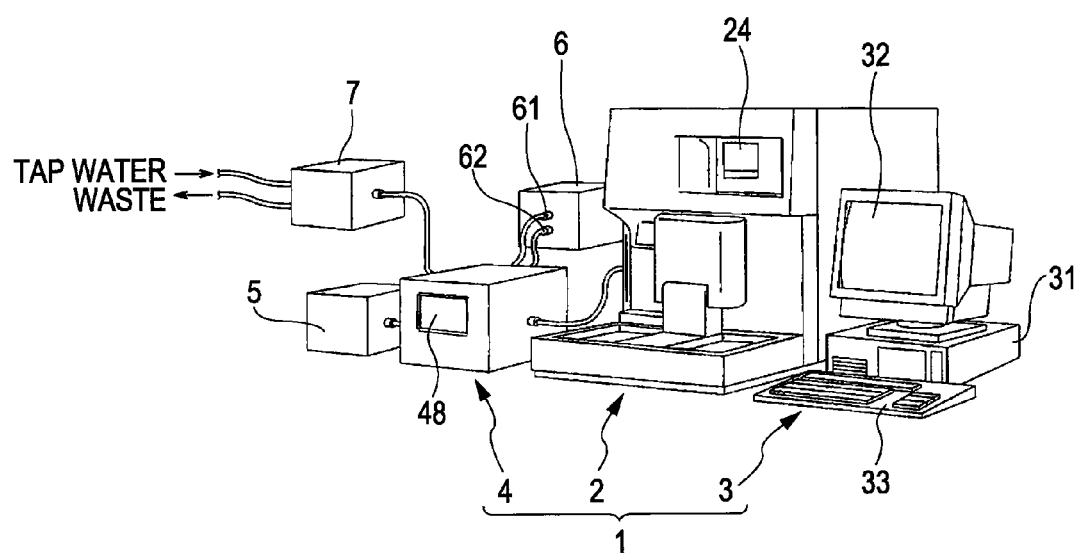
FIG. 1 is a perspective view showing the use of a sample processing apparatus provided with an embodiment of the reagent preparation apparatus of the present invention.

As shown in FIG. 1, the sample processing apparatus 1 is configured by a measuring unit 2 which has the function of performing measurements of blood, a data processing unit 3 which obtains analysis results by analyzing the measurement data output from the measuring unit 2, and a reagent preparation apparatus 4 for preparing reagent to be used in the processing of a sample. The measuring unit 2 is configured to measure leukocytes, reticulocytes and platelets in blood via flow cytometry. The measuring unit 2 is also configured to dilute the blood using the reagent prepared by the reagent preparation apparatus 4, and measure the leukocytes, reticulocytes, and platelets. Note that flow cytometry is a method for measuring particles (blood cells) by forming a sample flow that contains a measurement sample and irradiating the sample flow with laser light, then detecting the forward scattered light, side scattered light, and side fluorescent light emitted from particles (blood cells) in the measurement sample.

Figure 2:
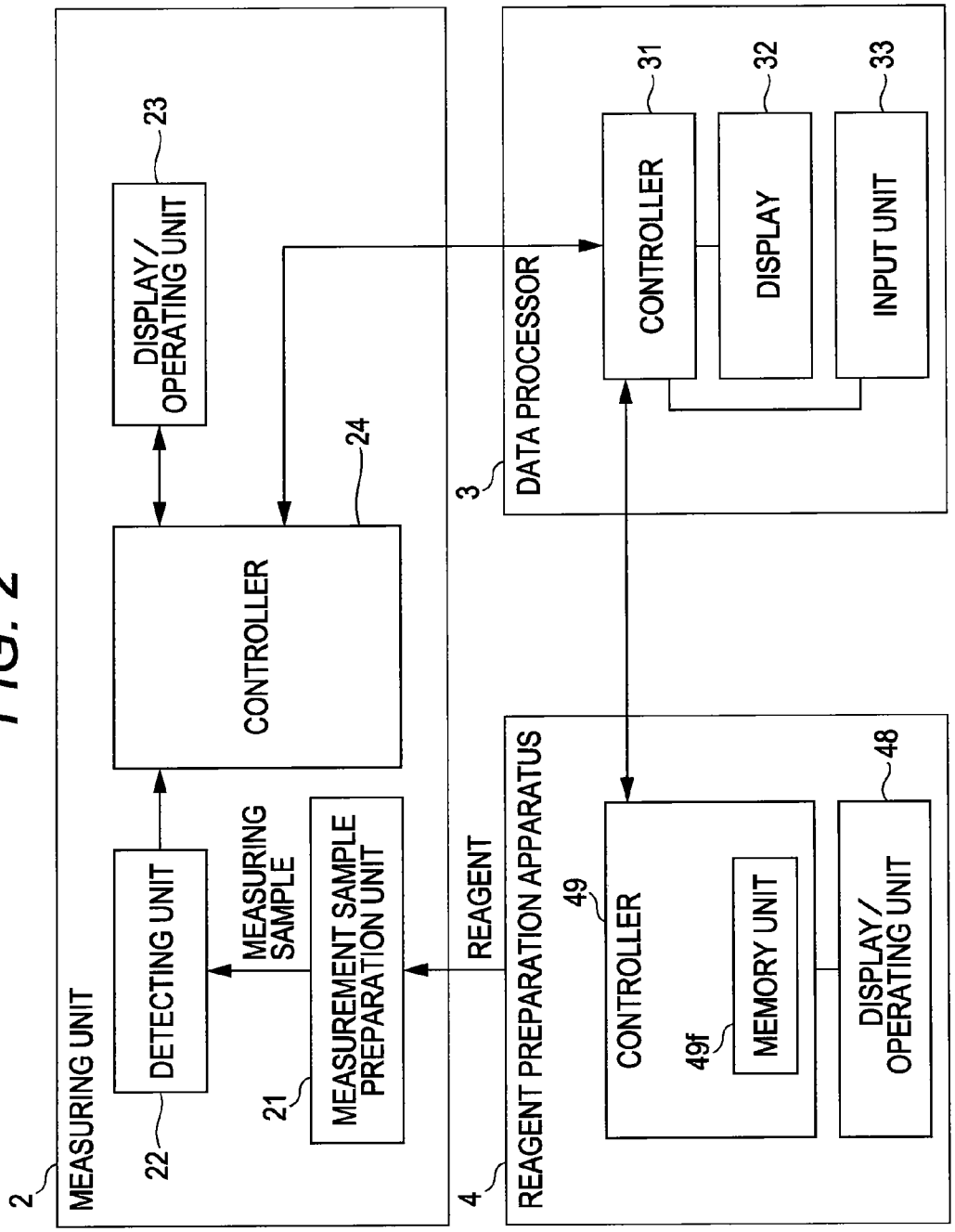
FIG. 2 is a block diagram showing the structure of a sample processing apparatus provided with an embodiment of the reagent preparation apparatus of the present invention.

As shown in FIG. 2, the measuring unit 2 is provided with a measurement sample preparation unit 21, detecting unit 22 for measuring the measurement sample, display/operating unit 23, and controller 24 for controlling the measuring unit 2. Note that the measuring unit 2 is an example of the sample processing unit of the present invention.

The measurement sample preparation unit 21 is configured to aspirate a predetermined amount of blood from a blood collection tube containing blood to be analyzed via an aspirating pipette (not shown in the drawing). The measurement sample preparation unit 21 is also configured to mix and react a stain with a predetermined amount of reagent supplied from the reagent preparation apparatus 4 to a predetermined amount of aspirated blood. In this way the measurement sample preparation unit 21 has the function of preparing a measurement sample suited for measurement to be performed by the detecting unit 22. The measurement sample preparation unit 21 is further configured to supply the prepared measurement sample together with a sheath fluid to the detecting unit 22. The measurement sample preparation unit 21 is additionally configured to wash the flow pass of the blood and measurement sample using a predetermined amount of reagent supplied from the reagent preparation apparatus 4. Note that the predetermined amount of reagent supplied from the reagent preparation apparatus 4 used to wash the flow pass is greater than the amount mixed with blood.

The detecting unit 22 has the functions of irradiating laser light on the sample flow containing the measurement sample passing through the interior of a sheath flow cell, and detecting the forward scattered light, side scattered light, and side fluorescent light emitted from the sheath flow cell. Information related to the size of particles (blood cells) in the measurement sample can be obtained from the forward scattered light. Information related to the interior of the particles (blood cells) in the measurement sample, such as the size of the nucleus and the like, can be obtained from the side scattered light. Information related to the degree of staining of particles (blood cells) in the measurement sample can be obtained from the side fluorescent light. The detecting unit 22 is configured to convert the received light signals to electric signals (detection signals) and output these electric signals to the controller 24.

The controller 24 performs predetermined arithmetic processing on the output signal from the detecting unit 22, and outputs the measurement data. The controller 24 has the function of controlling the measurement sample preparation unit 21 and the detecting unit 22. The controller 24 is also connected to the display/operating unit 23 and the data processing unit 3 The controller 24 has the further function of transmitting the arithmetic results (measurement data) to the data processing unit 3.

As shown in FIG. 1, the data processing unit 3 is a personal computer (PC), and has the functions of analyzing the measurement data of the measuring unit 2, and displaying the analysis results on a display unit 32. The data processing unit 3 includes a controller 31, display unit 32, and input unit (input device) 33. The controller 31 has the function of transmitting the measurement start signal, shutdown signal and the like to the measuring unit 2.

The reagent preparation apparatus 4 is provided to prepare reagent to be used by the measurement sample preparation unit 21 of the measuring unit 2. The reagent preparation apparatus 4 is configured to prepare reagent to be used in blood analysis by diluting a high concentration reagent to a desired concentration using RO water prepared by the RO water preparation unit 7 disposed outside the apparatus. RO water is a type of purified water from which the impurities have been removed by passage through an RO (reverse osmosis) membrane.

Figure 3:
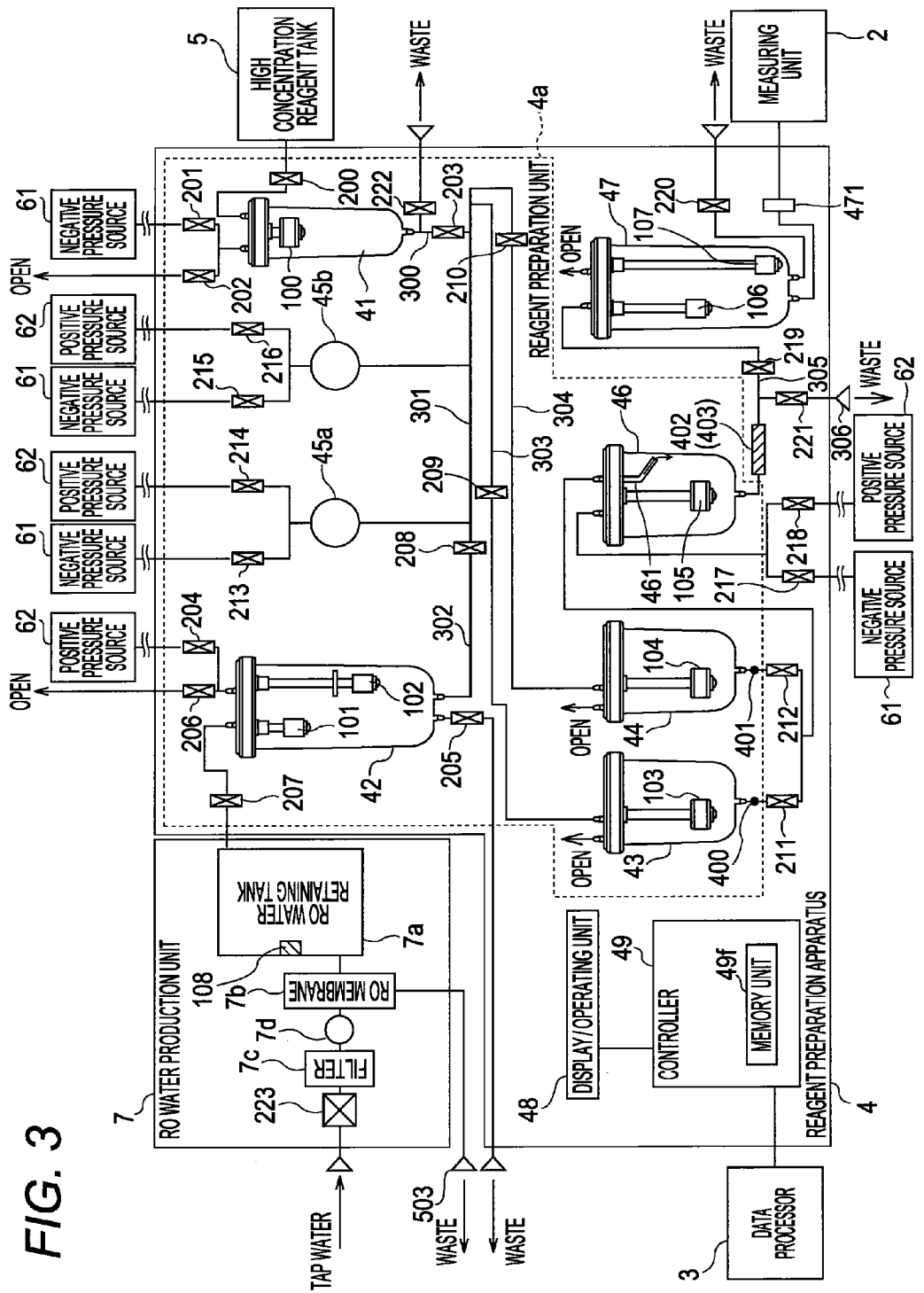
FIG. 3 is a block diagram showing the structure of an embodiment of the reagent preparation apparatus of the present invention.

As shown in FIG. 3, the reagent preparation apparatus 4 includes a high concentration reagent chamber 41, RO water chamber 42, two dilution chambers 43 and 44, two diaphragm pumps 45a and 45b, mixing chamber 46, supply chamber 47, display/operating unit 48, and a controller 49 to control the operation of each part of the reagent preparation apparatus 4. Note that the supply chamber 47 and the display/operating unit 48 are respectively examples of the reagent retaining unit and the display unit of the present invention. The reagent preparation unit 4a for preparing reagent is configured by a fluid circuit that includes the high concentration reagent chamber 41, RO water chamber 42, two dilution chambers 43 and 44, two diaphragm pumps 45a and 45b, and mixing chamber 46.

The reagent preparation apparatus 4 further includes a pneumatic unit 6 (refer to FIG. 1) disposed outside the housing, the reagent preparation apparatus 4 being configured to move each liquid within the apparatus using the negative pressure and positive pressure supplied from the pneumatic unit 6. The pneumatic unit 6 has a negative pressure source 61 for supplying a negative pressure, and a positive pressure source 62 for supplying a positive pressure.

The high concentration reagent chamber 41 is configured to receive high concentration reagent from the high concentration reagent tank 5. The high concentration reagent chamber 41 is provided with a float switch 100 which detects when a predetermined amount of high concentration reagent is accommodated within the chamber. The controller 49 controls the supply of high concentration reagent to the high concentration chamber 41 based on the detection result of the float switch 100. In the present embodiment, high concentration reagent is normally supplied until approximately 300 mL of reagent is retained in the high concentration reagent chamber 41.

The high concentration reagent chamber 41 is connected to the high concentration reagent tank 5 through an electromagnetic valve 200, and connected to the negative pressure source 61 of the pneumatic unit 6 through an electromagnetic valve 201. The high concentration reagent chamber 41 is opened to the atmosphere or closed by operating an electromagnetic valve 202. The high concentration reagent chamber 41 is also connected to a flow pass 301 for moving liquid from the diaphragm pump 45a (45b) to the diluting chamber 43 (44) through the flow pass 300 and the electromagnetic valve 203. The high concentration reagent chamber 41 is connected to a waste flow pass through an electromagnetic valve 222, and is configured to discharge the high concentration reagent contained therein to the waste flow pass.

The RO water chamber 42 is configured to supply RO water for diluting the high concentration reagent to the RO water preparation unit 7. The RO water chamber 42 is provided with float switches 101 and 102 for respectively detecting when the RO water within the chamber reaches an upper limit amount and a lower limit amount. The controller 49 controls the supply of RO water to the RO water chamber 42 based on the detection results of the float switches 101 and 102. In the present embodiment, the RO water chamber 42 stores RO water of approximately 300 mL or more but less than approximately 600 mL while the reagent preparation apparatus 4 is operating.

The RO water chamber 42 is connected to the RO water tank 7a of the RO water preparation unit 7 through an electromagnetic valve 207. The RO water chamber 42 is also connected to the positive pressure source 62 through an electromagnetic valve 204 and connected to the waste flow pass through an electromagnetic valve 205. In this way the RO water chamber 42 can discard the RO water within the chamber.

The RO water chamber 42 is opened to the atmosphere or closed by operating an electromagnetic valve 206. The RO water chamber 42 is further connected to the diaphragm pumps 45a and 45b through a flow pass 302 and an electromagnetic valve 208.

The diluting chambers 43 and 44 are respectively provided for diluting high concentration reagent with RO water. The diluting chamber 43 (44) accommodates approximately 300 mL of liquid (a mixture of high concentration reagent and RO water) delivered by the diaphragm pumps 45a and 45b. The diluting chamber 43 (44) is normally open to the atmosphere. The diluting chamber 43 (44) is connected to the flow pass 301 via the flow pass 303 (304) through an electromagnetic valve 209 (210). When the electromagnetic valve 209 is opened and the electromagnetic valve 210 is closed, liquid (RO water and high concentration reagent) is moved to the diluting chamber 43 through the flow pass 301 and flow pass 303. When the electromagnetic valve 210 is opened and the electromagnetic valve 209 is closed, liquid (RO water and high concentration reagent) is moved to the diluting chamber 44 through the flow pass 301 and flow pass 304.

The diluting chamber 43 (44) is connected to the mixing chamber 46 through an electromagnetic valve 211 (212). An air bubble sensor 400 (401) for detecting air bubbles passing through the flow pass is provided between the diluting chamber 43 (44) and the electromagnetic valve 211 (212). The complete discharge of all the liquid (mixture of RO water and high concentration reagent) in the diluting chamber 43 (44) is confirmed based on the detection result of the air bubble sensor 400 (401) and the detection result of the float switch 103 (104) provided within the diluting chamber 43 (44). When the diluting chamber 43 (44) is empty (that is, when all liquid within the chamber has been discharged), the controller 49 controls each part to supply RO water and high concentration reagent to the empty diluting chamber 43 (44).

The diaphragm pumps 45a and 45b are configured with mutually identical structures and perform similar operations simultaneously. The diaphragm pump 45a (45b) has the function of aspirating approximately 6 mL (approximately 12 mL total for two diaphragm pumps) of liquid (high concentration reagent or RO water) in each individual operation. The diaphragm pump 45a (45b) is connected to a negative pressure source 61 through an electromagnetic valve 213 (215) and connected to a positive pressure source 62 through an electromagnetic valve 214 (216).

The mixing chamber 46 accommodates approximately 300 mL of liquid. The mixing chamber 46 has a curved pipe 461, and liquids (high concentration reagent and RO water) moving from the diluting chamber 43 (44) flow through the pipe 461 into the mixing chamber 46 along the inner wall surface of the mixing chamber 46. In this way convection is produced within the mixing chamber 46 to mix the RO water and high concentration reagent.

When the float part of the float switch 105 provided within the mixing chamber 46 reaches the lower limit indicating that the chamber is empty, the controller 49 controls each part to supply approximately 300 mL of liquid mixture (reagent) from either the diluting chamber 43 or 44 to the mixing chamber 46. At this time, approximately 300 mL of liquid mixture may be alternately supplied from the diluting chamber 43 and diluting chamber 44 to the mixing chamber 46. In this way reagent preparation (dilution of high concentration reagent) can continue using the other chamber of the diluting chambers 43 or 44 while one or another of the diluting chambers 43 and 44 is moving liquid mixture to the mixing chamber 46. The mixing chamber 46 is also connected to the positive pressure source 62 through an electromagnetic valve 218 and connected to the negative pressure source 61 through an electromagnetic valve 217.

The supply chamber 47 has the function of storing a predetermined amount of reagent to be supplied to the measuring unit 2. The supply chamber 47 has a capacity of approximately 600 mL. The supply chamber 47 is provided with a float switch 106 for detecting when the residual reagent within the chamber reaches approximately 300 mL, and a float switch 107 for detecting when the residual reagent within the chamber is approximately depleted. The supply chamber 47 normally retains approximately 300 mL or more but less than approximately 600 mL of reagent of a desired concentration by the controller 49 controlling each part based on the detection result of the float switch 106. Note that the supply of reagent to the measuring unit 2 is stopped when the float switch 107 detects that the residual amount of reagent accommodated within the chamber is near zero.

The supply chamber 47 is connected to the mixing chamber 46 through an electromagnetic valve 219. The supply chamber 47 is configured to dispose of the reagent within the chamber for maintenance and the like by opening an electromagnetic valve 220. The supply chamber 47 is normally open to the atmosphere. The supply chamber 47 is also connected to the measuring unit 2 through a filter 471 which prevents contamination by impurities.

In the present embodiment, the flow pass 305, which is disposed between the mixing chamber 46 and the supply chamber 47, is provided with a conductance sensor 402 that measures the electrical conductance as a property of the reagent. The conductance sensor 402 includes a temperature sensor 403 for measuring the temperature of the reagent at the position at which the conductance sensor 402 is mounted. A waste flow pass 306 is connected between the conductance sensor 406 and the electromagnetic valve 219 through an electromagnetic valve 221. Therefore, a prepared reagent can be discarded through the electromagnetic valve 221 and the waste flow pass 306 before the prepared reagent is supplied to the supply chamber 47. Note that the conductance sensor 402 is an example of the measuring unit of the present invention.

The structure of the conductance sensor 402 and the structure of the conductance measuring circuit using the conductance sensor 402 are well known structures. The conductance measuring circuit and conductance sensor are disclosed, for example, in U.S. Patent Publication No. 2010/247383.

As shown in FIG. 1, the display/operating unit 48 is provided on the outer front surface of the reagent preparation apparatus 4. The display/operating unit 48 is a touch panel type liquid crystal display.

Figure 4:
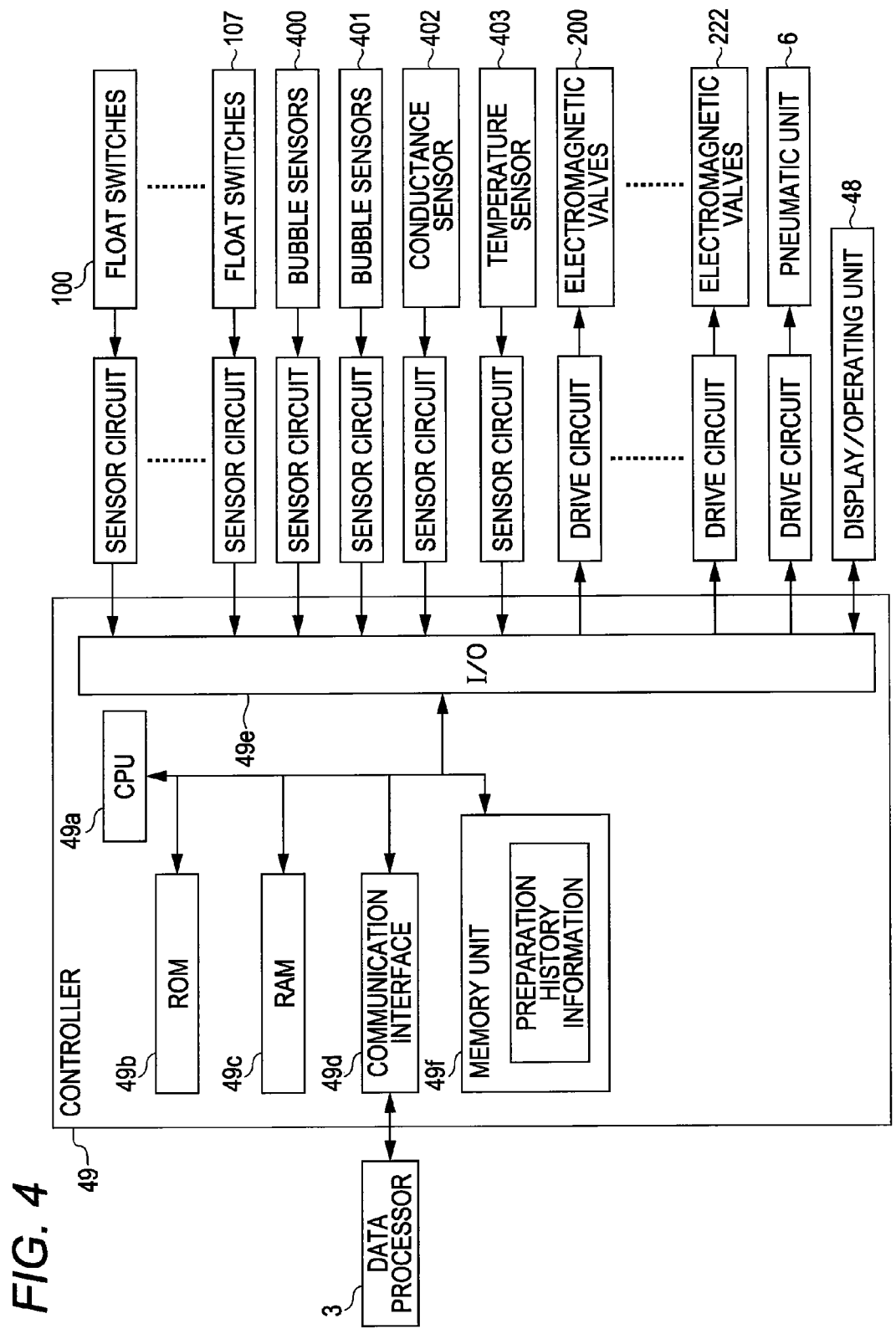
FIG. 4 is a block diagram illustrating the controller of an embodiment of the reagent preparation apparatus of the present invention.

As shown in FIG. 4, the controller 49 includes a CPU 49a, ROM 49b, RAM 49c, communication interface 49d connected to the data processing unit 3, I/O (input/output) interface 49e connected to each part of the reagent preparation apparatus 4, and memory unit 49f.

The CPU 49a is provided to execute a computer program stored in the ROM 49b and a computer program loaded in the RAM 49c. The CPU 49a is configured to use the RAM 49c as a work area when executing these computer programs.

The CPU 49a is further configured to receive a start instruction and shutdown instruction of the reagent preparation apparatus 4 from a user through the touch panel type display/operating unit 48, and recovery instruction during error stoppage of the reagent preparation unit 4a.

The communication interface 49d is configured to transfer error information to the data processing unit 3 so that the user can confirm an error warning generated within the reagent preparation apparatus 4.

The I/O unit 49e is configured to accept signals from the float switches 100 through 107, air bubble sensors 400 and 401, conductance sensor 402 and temperature sensor 403 through each sensor circuit. The I/O unit 49e outputs signals to each drive unit to control the actuation of the pneumatic unit 6 and electromagnetic valves 200 through 222. The I/O unit 49e receives signals corresponding to user instructions from the touch panel type display/operating unit 48, and outputs image signals to the display/operating unit 48.

The memory unit 49f is a nonvolatile memory. In the present invention, the memory unit 49f is configured to store preparation history information for each reagent prepared by the reagent preparation apparatus 4. The preparation history information included the date and time of reagent preparation, the measured temperature of the reagent by the temperature sensor 403, the measurement result (conductance) of the reagent by the conductance sensor 402, and suitable/unsuitable determination result which will be described later, for each prepared reagent.

As shown in FIG. 3, the RO water preparation unit 7 is configured to prepare RO water as a diluting liquid for diluting high concentration reagent using tap water. The RO water preparation unit 7 includes a water storage tank 7a for storing RO water, RO membrane 7b, and filter 7c for removing impurities contained in the tap water. The RO water preparation unit 7 further includes a high pressure pump 7d for pressurizing the water so that the water molecules are forced to pass through the RO membrane 7b, and an electromagnetic valve 223 for controlling the supply of tap water.

The RO water preparation unit 7 is configured to deliver tap water to the filter 7c by opening the electromagnetic valve 223. By driving the high pressure pump 7d, the RO water preparation unit 7 forces the water filtered through the filter 7c to then pass through the membrane 7d at high pressure. The RO water preparation unit 7 then retains a predetermined amount of RO water in the RO water retaining tank 7a based on the detection result of the float switch 108.

In the present embodiment, the controller 49 determines whether the prepared reagent is suited or unsuited for measurement (sample processing) by the measuring unit 2 based on the measurement result of the conductance sensor 402.

The controller 49 calculates the conductance of the reagent converted to a predetermined standard temperature (25 degrees) based on the temperature of the reagent measured by the temperature sensor 403 and the conductance of the reagent flowing through the flow pass 305 as measured by the conductance sensor 402.

When measuring the conductance of the reagent, the controller 49 repeats the measurement several times (30 times in the present embodiment) over a predetermined time (3 seconds in the present embodiment). The controller 49 deletes both ends of a plurality of obtained data, and compares the processed data to a predetermined standard range. Note that deletion of both ends of the plurality of data means, for example, that the upper order five data and lower order 20 data are not used.

The controller 49 makes the suitable/unsuitable determination of the reagent by comparing the magnitude of the calculated reagent conductance and several conditions. The suitable/unsuitable conditions correspond to a plurality of predetermined conductance ranges. The suitability of the reagent is determined each time reagent is prepared. That is, the conductance of the reagent is measured as the reagent supplied from the mixing chamber 46 passes through the conductance sensor 402 in the flow pass 305, and the suitability of the reagent is determined based on the degree of measured conductance. The controller 49 performs appropriate processing (supply reagent to the supply chamber 47, discard reagent and the like) according to whether the measured conductance of the reagent meets any one of a plurality of conditions.

Figure 5:
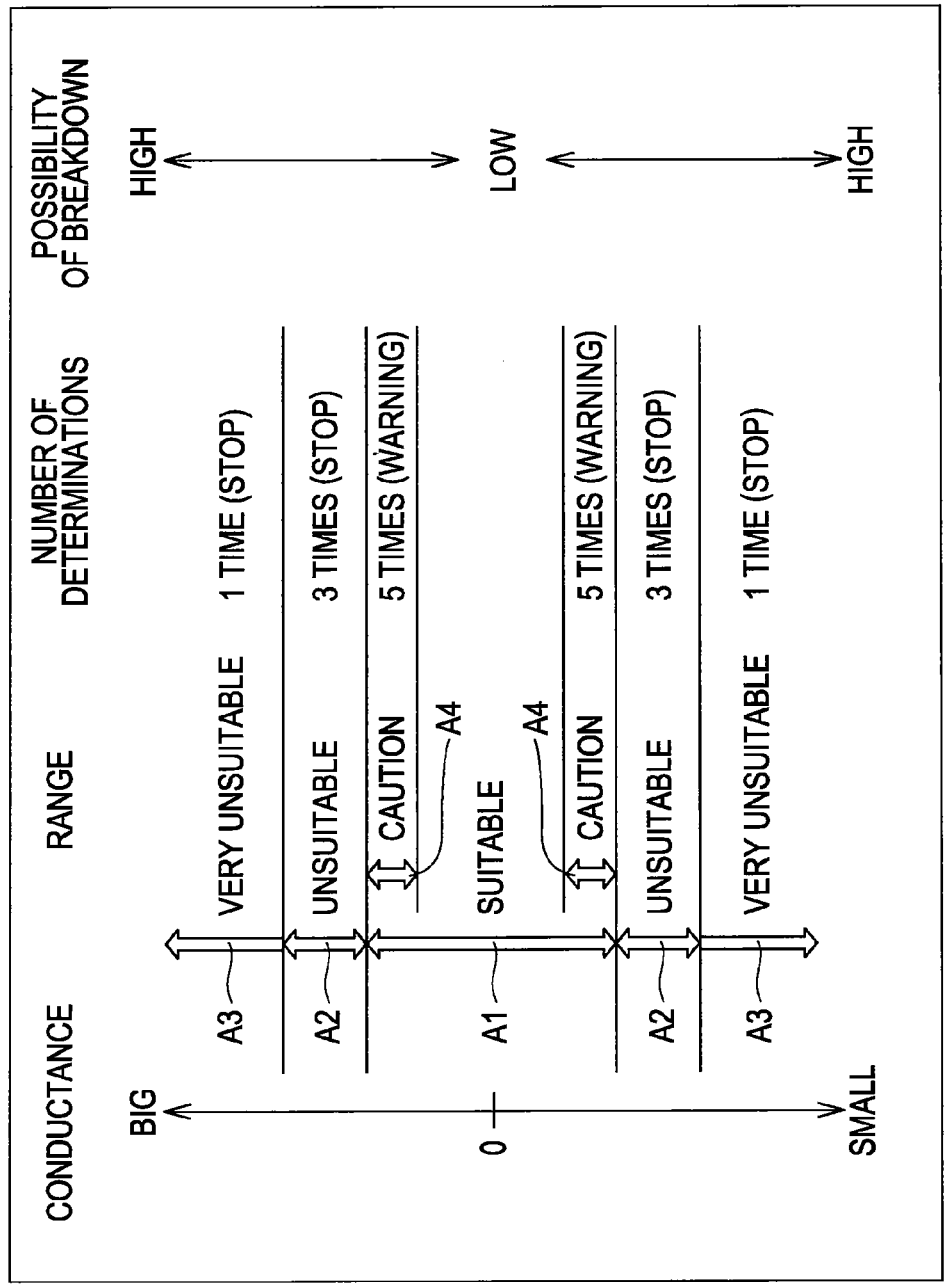
FIG. 5 illustrates the content of the suitable/unsuitable determination performed by the controller of the embodiment of the reagent preparation apparatus of the present invention.

As shown in FIG. 5, four ranges of reagent conductance (ranges A1 through A4) are used in the present embodiment to determine reagent suitability.

The conductance range indicated by range A1, which is centered on the optimum value 0 of conductance, is a "suitable" range. When the measurement result of the conductance sensor 402 (measured reagent conductance) is within the range A1, the controller 49 moves this quality-confirmed reagent to the supply chamber 47 (refer to FIG. 3). In this case, the controller 49 determines the reagent is suitable since the reagent conductance is within the standard range.

When the measurement result of the conductance sensor 402 is not within the range A1 (that is, the measurement result is within either range A2 or range A3, which are described later), the reagent is discarded to the waste section 306 (refer to FIG. 3).

As shown in FIG. 5, the conductance range indicated by range A2 is distributed outside both ends the range A1, and is an "unsuitable" range. The conductance range indicated by range A3 is distributed outside both ends of range A2, and is a "very unsuitable" range. The controller 49 determines a conductance is unsuitable when the measurement result is not within the range A1 but is within the range A2. The controller 49 determines a conductance very unsuitable when the measurement result is neither within range A1 or range A2 but is within range A3. In the "unsuitable" range (range A2) and "very unsuitable" range (range A3), there is a possibility that a failure (breakdown) of the reagent preparation apparatus 4 may be occurring since normal reagent preparation is not being performed. Therefore, the controller 49 stops the operation of the reagent preparation unit 4a when an "unsuitable" (range A2) and "very unsuitable" (range A3) determination is returned over several determinations.

In the present embodiment, the number of determinations for stopping the operation of the reagent preparation unit 4a is set to a different number according to the degree of unsuitability. The number of determinations of unsuitability required to stop the operation is set at three times. That is, the controller 49 discards the unsuitable reagent to the waste section 306 and continues reagent preparation until the unsuitability determination has been made up to three times (one or two times). The controller 49 discards the unsuitable reagent to the waste section 306 and stops the operation of the reagent preparation unit 4a when an unsuitable reagent determination has been returned three times.

The number of "very unsuitable" (range A3) reagent determinations required to stop the operation is less than the number of "unsuitable" reagent determinations (which is three times), that is, one time. When a "very unsuitable" reagent determination is returned, the controller 49 discards the reagent to the waste section 306 and immediately stops the reagent preparation unit 4a. That is, there is concern of severe breakdown (massive failure) of some type when the measurement result exceeds the tolerance range A1 of usable reagent, and also exceeds the normally unsuitable range A2. Therefore, the controller 49 stops the reagent preparation unit 4a after a single "very unsuitable" reagent determination.

Within range A1, the conductance range indicated by range A4 near the boundary with range A2 is the "caution" determination range. When the measurement result is within the range A4 (no failure discernible at the current time), there is a high possibility of a future failure even though the measurement result is within the range A1. Therefore, the controller 49 makes a cautionary determination when the measurement result meets the condition of being within the range A4.

The controller 49 is configured to alert the user by displaying a cautionary warning on the display/operating unit 48 when the cautionary determination is returned a predetermined number of times. In the present embodiment, the number of cautionary determinations required for a warning message to be displayed is set at five times. That is, the controller 49 displays a warning message when five cautionary determinations occur. Note that prepared reagent is moved to the supply chamber 47 even when a cautionary determination is made since the measurement result is within the range A1.

The controller 49 displays error information (refer to FIG. 8) on the display/operating unit 48 when the operation of the reagent preparation unit 4a is stopped (when an "unsuitable" determination is returned three times or a "very unsuitable" determination is returned once). The controller 49 receives a recovery instruction from the user on the error detail screen (refer to FIG. 10) displayed on the display/operating unit 48. When the user inputs a recovery instruction, the controller 49 performs a predetermined automatic washing operation as a recovery action, and thereafter cancels the operation stoppage of the reagent preparation unit 4a.

The controller 49 stores the number of apparatus stoppages in the memory unit 49f. When the apparatus stoppage has continued to occur a predetermined number of times, the controller 49 displays a message indicating failed recovery (refer to FIGS. 11 and 12) on the display/operating unit 48 and ends the reagent preparation process (recovery failure error). The recovery failure message includes instructions to contact the apparatus maintenance staff.

In the present embodiment, the number of apparatus stoppages is set at two times. After the operation of the reagent preparation unit 4a has been stopped and the recovery operation performed (automatic washing operation), when the unsuitable determination occurs again (three times) or a very unsuitable determination occurs (one time) and the reagent preparation operation is stopped, the controller 49 halts the operation while the unrecoverable error condition continues.

Details of the screen display of the display operating unit 48 related to the unsuitable determination by the controller 49 are described below with reference to FIGS. 6 through 12.

Under normal operating conditions, the status display screen D1 shown in FIG. 6 is displayed on the display/operating unit 48. In the normal operating condition, an estimate of the residual amount of high concentration reagent is displayed via icon D12 in the information display area D11, and the lot number, replacement date, and expiration date of the high concentration reagent are also displayed.

A select button D13, reagent button D14, preparation interrupt button D15, and shutdown button D16 are provided in the lower part of the status display screen D1. Upon touch input of each button, the controller 49 performs the corresponding process (shutdown, preparation interrupt process and the like) and displays information (reagent preparation history and the like). A help button D17 is provided in the upper right corner of the status display screen D1 to display information at predetermined times, such as when an error occurs.

The preparation history display screen D2 shown in FIG. 7 is displayed by touching the select button D13 and selecting the reagent preparation history item (not shown) from the menu. The preparation history display screen D2 displays the reagent preparation history information stored in the memory unit 49f.

As shown in FIG. 7, in the history display area D21 in the preparation history display screen D2, the reagent preparation date and time, suitable/unsuitable determination result by the controller 49 ("result" column D22), temperature measured by the temperature sensor 403, and measurement result (conductance) measured by the conductance sensor 402 are displayed.

"OK" in the result column D22 of the history display area D21 indicates a determination of "suitable" for that reagent. "NG" indicates "unsuitable" determination, "WA" indicates "cautionary" determination, and "BD" indicates "very unsuitable" determination.

Figure 8:
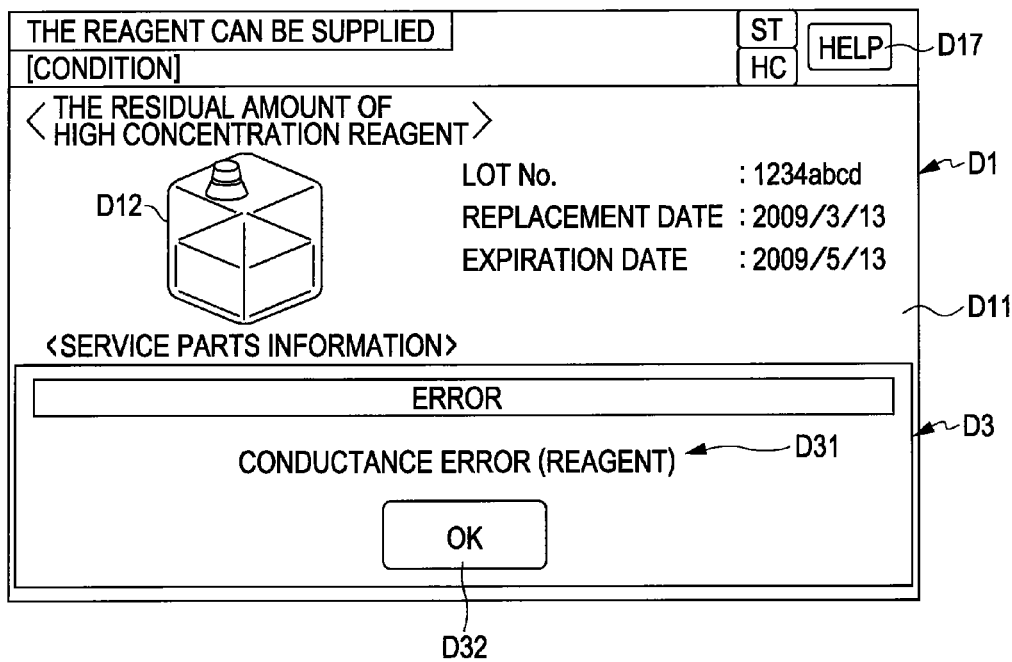
FIG. 8 is a screen view illustrating the error display part (electric conductance anomaly) displayed on the display/operating unit of the embodiment of the reagent preparation apparatus of the present invention.

As described above, when the controller 49 makes an "unsuitable" determination three times or a "very unsuitable" determination once during the execution of the reagent preparation process, the controller 49 stops the reagent preparation operation of the reagent preparation unit 4a. In this case, the error display area D3 is displayed on the status display screen D1, as shown in FIG. 8. Note that in this case the controller 49 may alert the user that an error has occurred via a continuous audible alarm from speakers (not shown in the drawing).

An error message D31 and OK button D32 are displayed in the error display area D3. When the OK button D32 is touched, the error display area D3 is canceled and the display returns to the status display screen D1 of FIG. 6. In this case, the help button D17 in the upper right corner of the status display screen D1 is touched, the error list display screen D4 is displayed as shown in FIG. 9.

Figure 9:
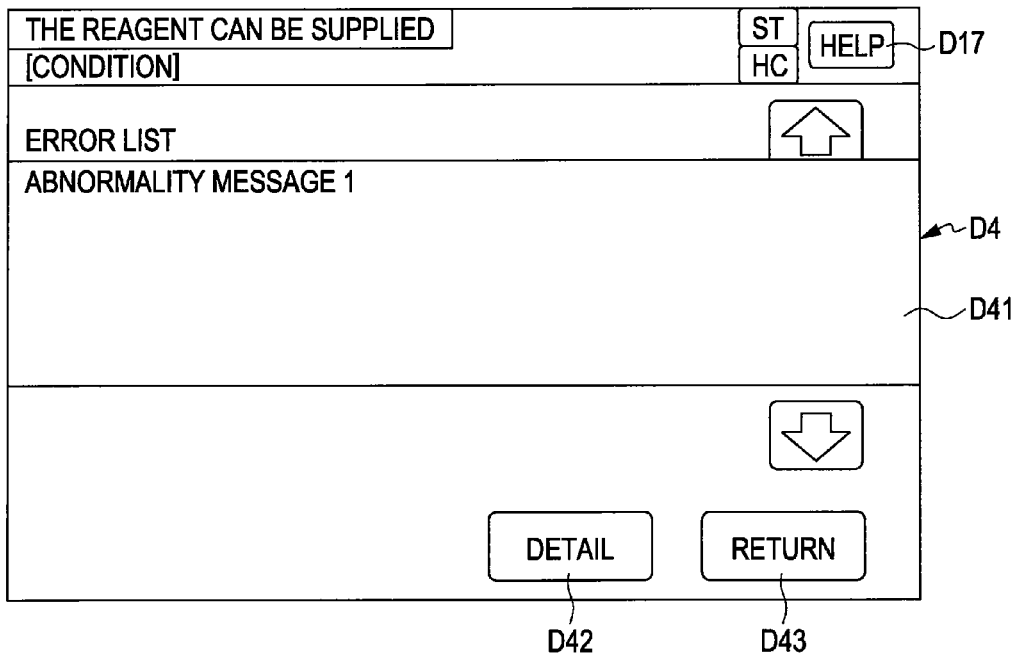
FIG. 9 is a screen view illustrating the error list display screen displayed on the display/operating unit of the embodiment of the reagent preparation apparatus of the present invention.

As shown in FIG. 9, a list area D41, detail button D42, and return button D43 are displayed in the error list display screen D4. Errors are displayed top to bottom in the priority sequence in the list area D41. When the apparatus is stopped as a result of three "unsuitable" determinations or one "very unsuitable" determination, an abnormality message 1 is displayed in the list area D41 as shown in FIG. 9. When the detail button D42 is touched with the item displayed in the list area D41, the display is switched to the error detail screen D5 shown in FIG. 10.

A detail display area D51, OK button D52, and cancel button D53 are displayed in the error detail screen D5. Detailed information of the error is displayed in the detail display area D51.

Figure 10:
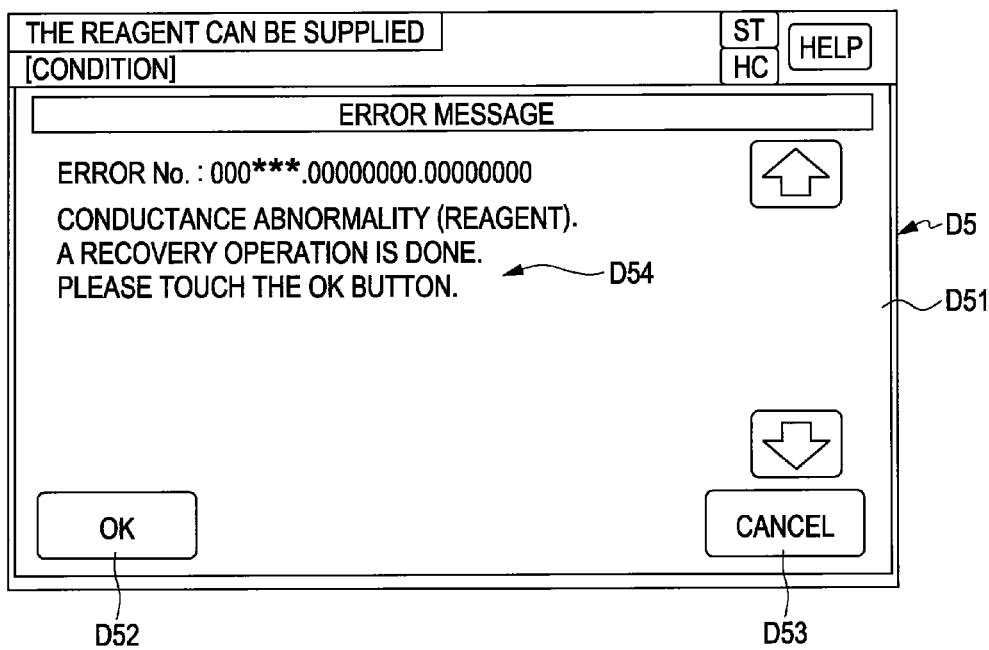
FIG. 10 is a screen view illustrating the error detail screen (electric conductance anomaly) displayed on the display/operating unit of the embodiment of the reagent preparation apparatus of the present invention.

Note that the error detail screen D5 of FIG. 10 shows an example of error information (abnormal conductance) during a first apparatus stoppage in response to an "unsuitable" determination (three consecutive times) or "very unsuitable" determination (once) by the controller 49. An error message D54 indicating an error has occurred (conductance abnormality) and recovery operation is displayed in the detail display area D51. The controller 49 awaits the reception of a recovery operation start instruction via input from the OK button D52. When the user touches the OK button D52, the controller 49 executes the automatic washing operation as a recovery operation.

Figure 11:
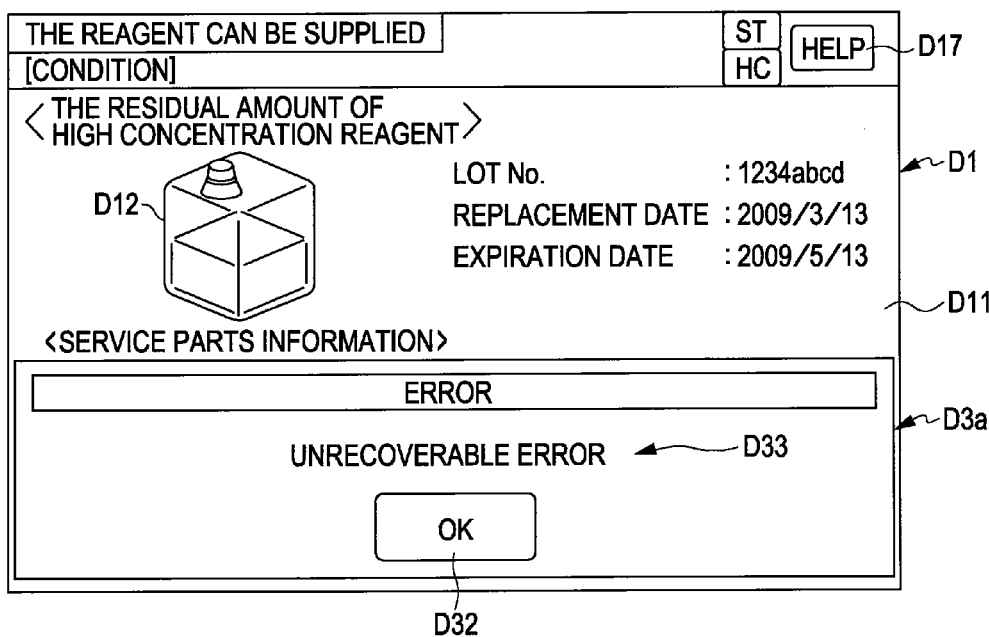
FIG. 11 is a screen view illustrating the error display part (unrecoverable error) displayed on the display/operating unit of the embodiment of the reagent preparation apparatus of the present invention.

The error display D3a shown in FIG. 11 is displayed when the apparatus has been stopped two times consecutively (unrecoverable error) by an "unsuitable" determination (three times) or a "very unsuitable" determination (one time). In this case, an error message D33 indicating an unrecoverable error is displayed instead of the error message D31 of FIG. 8. In the case of an unrecoverable error, the error detail screen D5a shown in FIG. 12 is displayed.

Figure 12:
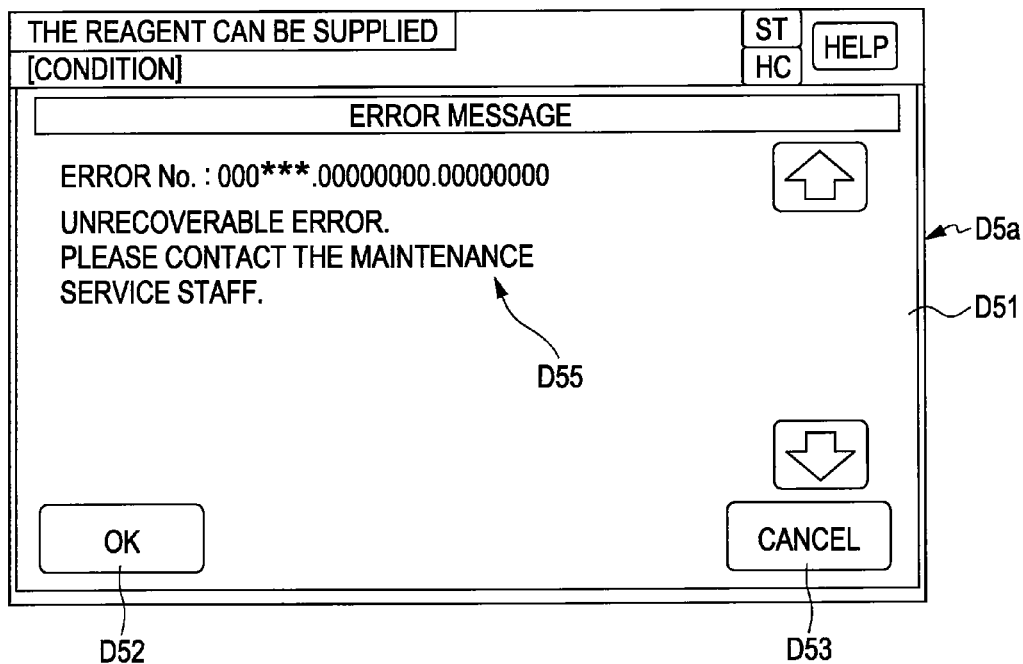
FIG. 12 is a screen view illustrating the error detail screen (unrecoverable error) displayed on the display/operating unit of the embodiment of the reagent preparation apparatus of the present invention.

In the detailed error screen D5a shown in FIG. 12, an error message D55 is displayed on the detail display area D51, the error message D55 indicating an unrecoverable anomaly occurred (unrecoverable error), and instructions to contact the maintenance service staff. In this case, the operation of the reagent preparation unit 4a is stopped during the error condition and a recovery operation is not executed even if the user touches the OK button D52.

Figure 13:
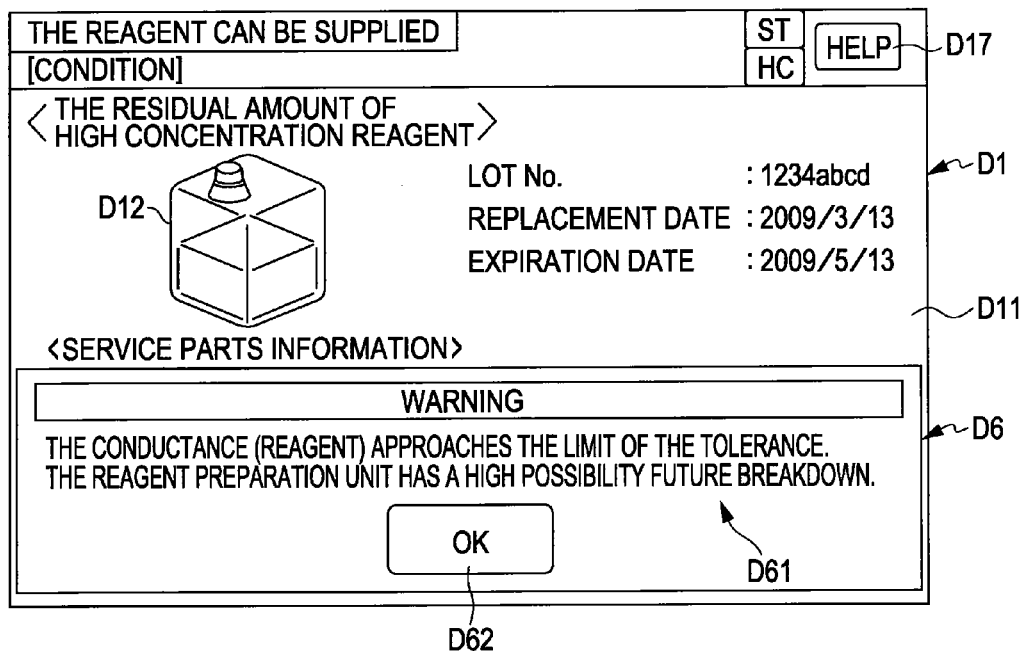
FIG. 13 is a screen view illustrating the warning display part displayed on the display/operating unit of the embodiment of the reagent preparation apparatus of the present invention.

Note that a "cautionary" determination is made when five consecutive "unsuitable" determination have occurred, and a warning (alert) shown in FIG. 13 is displayed on the display unit D6. Unlike when the error display D3 shown in FIG. 8 is displayed, in this case the reagent preparation operation continues without stopping the apparatus.

As shown in FIG. 13, a warning message D61 and an OK button D62 are displayed in the warning display part D6. When the OK button D62 is touched, the warning display D6 is canceled and the display returns to the status display screen D1 of FIG. 6. The history of "cautionary" determinations (five consecutive times) that caused the warning display can be confirmed in the history display area D21 in the preparation history display screen D2 shown in FIG. 7. Note that since the warning display will be different according to the causing the stoppage of the apparatus, the warning display may include an audible alarm accompanying the display or without an audible alarm.

The reagent preparation operation of the reagent preparation apparatus 4 of the present embodiment is described below with reference to FIGS. 3, 5, 8, and 10 through 15.

Figure 14:
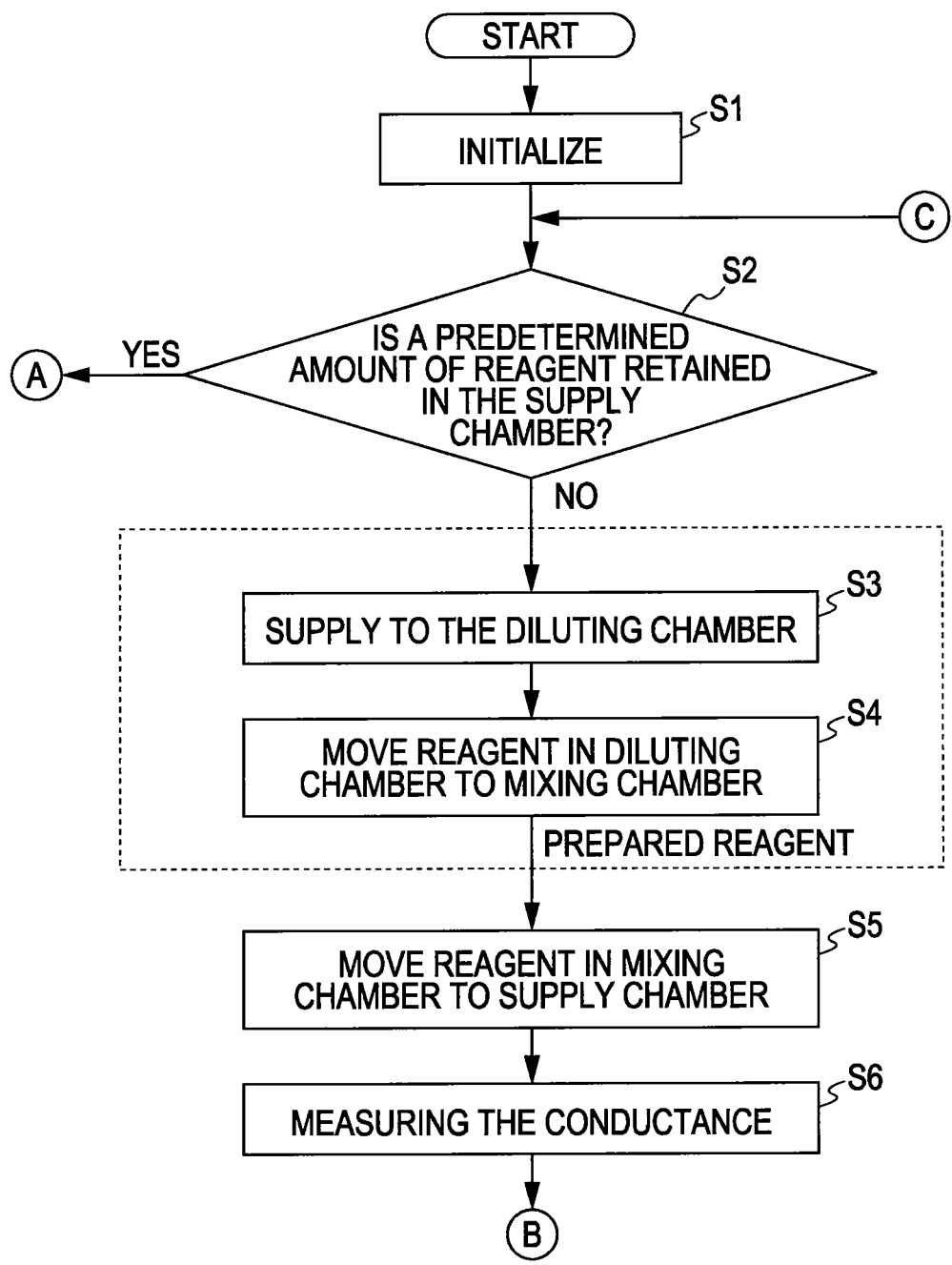
FIG. 14 is a flow chart illustrating the first half of the reagent preparation operation of the embodiment of the reagent preparation apparatus of the present invention.

In step S1 of FIG. 14, the controller 49 initializes a computer program stored in the ROM 49b. In step S2, the controller 49 determines whether a predetermined amount (approximately 300 mL or more but less than 600 mL) of reagent is retained in the supply chamber 47. When the predetermined amount of reagent is retained in the supply chamber 47, the process moves to step S16 of FIG. 15. When the predetermined amount of reagent is not retained in the supply chamber 47, however, the process mode to step S3 and the controller 49 starts the reagent preparation process of the reagent preparation unit 4a.

In step S3, the controller 49 supplies the high concentration reagent within the high concentration reagent chamber 41 and the RO water within the RO water chamber 42 to the diluting chamber 43 (44).

Specifically, approximately 12 mL of high concentration reagent (approximately 6 mL from each diaphragm pump) is aspirated from the high concentration reagent chamber 41 to the diaphragm pumps 45a and 45b using the negative pressure of the negative pressure source 61. Thereafter, the aspirated concentrated reagent is moved from the diaphragm pumps 45a and 45b to the target diluting chamber 43 or 44. Similarly, approximately 288 mL of RO water (approximately 12 mL times 24 times) are moved from the RO water chamber 42 to the target diluting chamber 43 or 44. In this way approximately 300 mL of a liquid mixture (reagent) consisting of about 288 mL of RO water and about 12 mL of concentrated reagent is moved to the diluting chamber 43 or 44. These operations are performed by the controller 49 controlling the operation of the electromagnetic valves 203, 208, and 213 through 216, and operating either electromagnetic valve 209 or 210 as a flow pass selector.

In step S4 of FIG. 14, the reagent within the diluting chamber 43 (44) is supplied to the mixing chamber 46. As shown in FIG. 3, the controller 49 opens the electromagnetic valve 217 and closes either the electromagnetic valve 211 or 212 corresponding to the diluting chamber 43 or 44 that supplies the liquid. In this way the reagent is moved to the mixing chamber 46 by the negative pressure of the negative pressure source 61. The supplied reagent is then uniformly mixed in the mixing chamber 46.

In step S5 of FIG. 14, the reagent starts to move from the mixing chamber 46 to the supply chamber 47. As shown in FIG. 3, the controller 49 closes the electromagnetic valve 217 and opens the electromagnetic valve 18. In this way the reagent within the mixing chamber 46 flows into the flow pass 305 via the positive pressure of the positive pressure source 62. In step S6 of FIG. 14, the conductance sensor 402 measures the conductance of the reagent flowing into the flow pass 305, and the temperature sensor 403 measures the temperature of the reagent.

Figure 15:
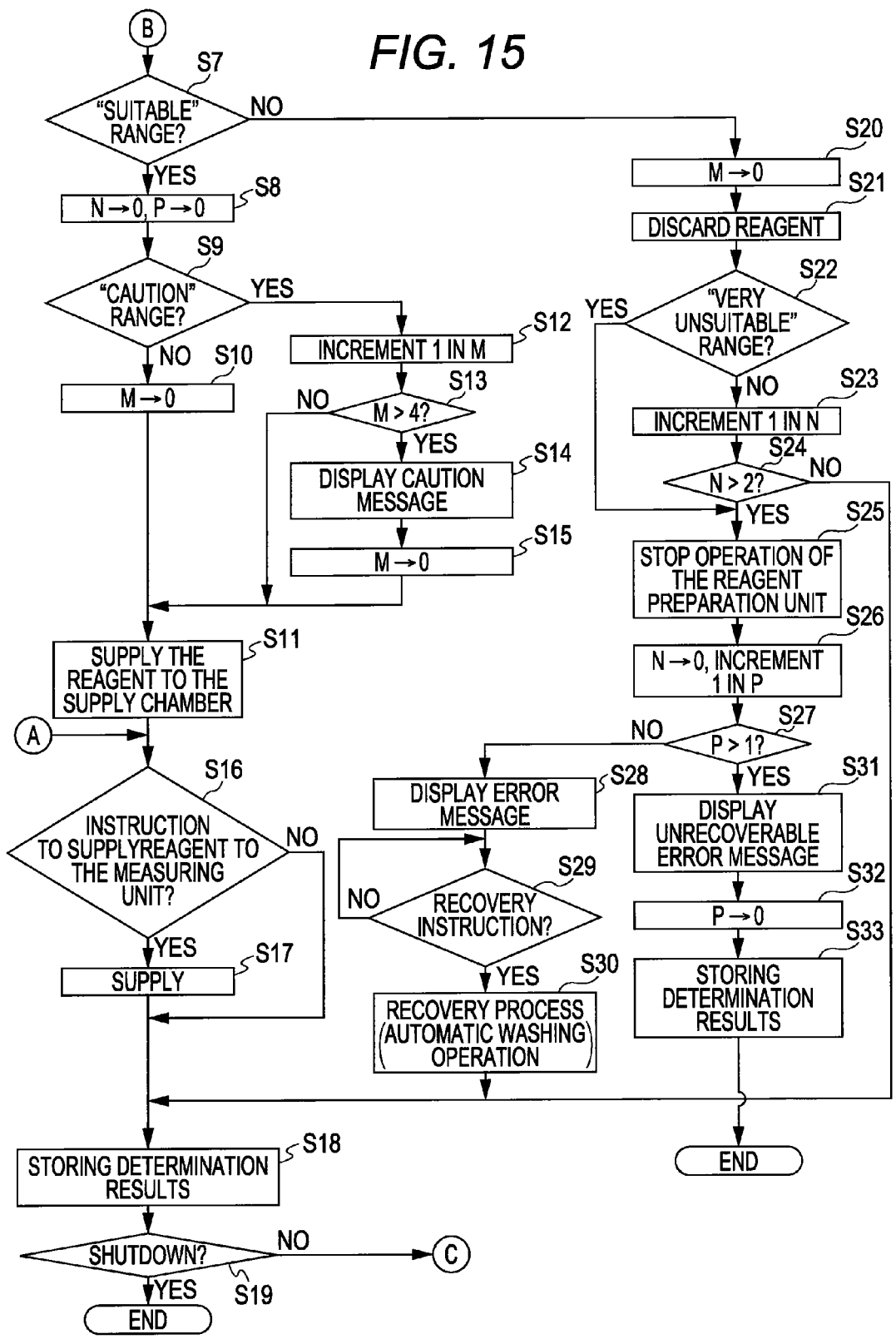
FIG. 15 is a flow chart illustrating the second half of the reagent preparation operation of the embodiment of the reagent preparation apparatus of the present invention.

In step S7 of FIG. 15 in the present embodiment, the controller 49 determines whether the measurement result (conductance) of the conductance sensor 402 is within the range A1 ("suitable" range; refer to FIG. 5).

When the measurement result is within the range A1, the process continues to step S8 and the controller 49 resets the value of variable N, which indicates the number of "unsuitable" determinations, to zero. The controller 49 then resets to zero the value of the variable P, which indicates the number of stoppages of the preparation operation of the reagent preparation unit 4a due to an "unsuitable" determination or "very unsuitable" determination.

In step S9, the controller 49 determines whether the measurement result (conductance) is within the range A4 ("caution" range; refer to FIG. 5).

When the measurement result is outside the range A4, the controller 49 moves the process to step S10 and resets to zero the value of the variable M which indicates the number of "caution" determinations.

When the measurement result is within the range A4, however, the controller 49 makes a "caution" determination regarding the result of the "suitable/unsuitable" determination. Continuing to step S12, the controller 49 increments the value of the "caution" determination number M by [1]. In step S13, the controller 49 determines whether the value of the number of "caution" determinations M is greater than [4].

When the value of M is [4] or less, the process moves to step S11. When the result of the incrementation in step S12 is that the value of the "caution" determination number M becomes [5], the process moves to step S13 and the controller 49 displays on the display/operating unit 48 a warning message D62 (warning display D6; refer to FIG. 13) representing the possibility of a future failure. In step S15, the controller 49 resets the value of the "caution" determination number M to [0], and the process moves to step S11.

In step S11, the reagent is supplied from the supply chamber 47. That is, when the measurement result of the reagent flowing through the flow pass 305 in step S7 is determined to be within the range A1, the controller 49 closes the electromagnetic valve 221 (refer to FIG. 3) and opens the electromagnetic valve 219 (refer to FIG. 3). As shown in FIG. 3, the reagent of the flow pass 305 is thus supplied to the supply chamber 47. The measurement by the conductance sensor 402 and the suitable/unsuitable determination by the controller 49 end when the reagent from the mixing chamber 46 flows through the flow pass 305 and reaches the electromagnetic valves 219 and 221. Therefore, when the measurement result (measured reagent conductance) of the conductance sensor 402 is within the range A1, the reagent is not stopped in the flow pass 305 and is supplied to the supply chamber 47.

As shown in FIG. 15, when the supply of reagent to the supply chamber 47 ends, or when a predetermined amount of reagent is determined to reside in the supply chamber 47 in step S2 (refer to FIG. 14), the controller determines whether an instruction to supply reagent to the measuring unit 2 has been received in step S16. When an instruction to supply reagent to the measuring unit 2 has not been received, the process moves to step S18. When an instruction to supply reagent to the measuring unit 2 has been received, the reagent in the supply chamber 47 is moved to the measuring unit 2 in step S17.

In step S18, the reagent suitable/unsuitable determination results ("suitable" determination, "caution" determination, "unsuitable" determination, "very unsuitable" determination) are stored in the memory unit 49f. Note that in step S18 the measurement results (conductance) of the conductance sensor 402, measurement results of the temperature sensor 40, reagent preparation date/time included in the preparation history information are also stored in the memory 49f in addition to the suitable/unsuitable determination results.

In step S19, the controller 49 determines if there is a shutdown instruction. When there is no shutdown instruction, the process returns to step S2. When there is a shutdown instruction, the controller 49 performs a predetermined shutdown process and the reagent preparation operation ends.

In step S15, when the controller 49 determines that the measurement result is not within the range A1 ("suitable" range), the measurement result of the suitable/unsuitable determination is either "unsuitable" or "very unsuitable".

When the process moves to step S20, the controller 49 resets the value of the caution determination frequency M to [0].

In step S21, the controller 49 discards the reagent for which the measurement result is not within the range A1 to the waste section 306. That is, the controller 49 closes the electromagnetic valve 219 and opens the electromagnetic valve 221 to move the reagent from the flow pass 305 to the waste section 306 via the positive pressure of the positive pressure source 62, as shown in FIG. 3. Thus, the reagent with the unsuitable measurement result is not supplied to the supply chamber 47, but rather is discarded to the waste section 306.

In step S22 of FIG. 15, the controller 49 determines whether the measurement result (conductance) of the conductance sensor 402 corresponds to the range A3 ("very unsuitable" range; refer to FIG. 5). That is, the controller 49 determines whether the measurement result is within the range A3 (refer to FIG. 5). When the measurement result is not within the range A3, the controller 49 makes a suitable/unsuitable determination that the measurement result "unsuitable". When the measurement result is within the range A3, the controller 49 makes a suitable/unsuitable determination that the measurement result is "very unsuitable".

When the determination result is "unsuitable", the controller 49 increments the value of the unsuitable determination frequency N by [1] in step S23. In step S24, the controller 49 determines whether the value of the unsuitable determination frequency N is [2] or greater.

When the value of N is less than [2], the process moves to step S18 and the controller 49 stores the determination result (preparation history information) in the memory unit 49f. Therefore, the controller 49 continues the reagent preparation operation of the reagent preparation unit 4a until the unsuitable determination frequency N is [2].

When a "very unsuitable" determination is made in step S22, or when the unsuitable determination frequency N becomes [3] (when N is greater than 2), the process moves to step S25.

In step S225, the controller 49 stops the operation of the reagent preparation unit 4a. In step S26, the controller 49 resets the unsuitable determination frequency N to [0], and increments the value of the variable P, which represents the apparatus stoppage frequency, to [1].

In step S27, the controller 49 determines whether the value of the apparatus stoppage frequency P is [1] or greater. When the apparatus stoppage frequency P is [1], the process continues to step S28 and the controller 49 displays an error message D31 (error display D3; refer to FIG. 8) on the display/operating unit 48. The controller 49 also displays an error message D54 (error detail screen D5; refer to FIG. 10) on the display/operating unit 48.

In step S29, the controller 49 determines whether there is recovery instruction via user input. Specifically, the controller 49 determines whether the OK button D52 has been touched on the error detail screen D5 of FIG. 10. The controller 49 repeats the determination of step S29 until a recovery instruction is received, and awaits user operation input.

As shown in FIG. 15, when a recovery instruction is received, the process moves to step S30 and the controller 49 performs the automatic washing operation as a recovery operation.

As shown in FIG. 3, in the automatic washing operation the controller 49 opens the electromagnetic valves 204 and 205, and discharges the RO water in the RO water chamber 42 via the positive pressure of the positive pressure source 62. The controller 49 then closes the electromagnetic valves 204 and 205, opens electromagnetic valves 206 and 207, and replaces the RO water from the RO water preparation unit 7 to the RO water chamber 42. The controller 49 then washes the diluting chambers 43 and 44, and the mixing chamber 46. That is, the controller 49 discards all the reagent retained in the diluting chambers 43 and 44 and the mixing chamber 46 while the operation of the apparatus is stopped and moves the reagent to the waste section 306. Thereafter, the controller 49 supplies the newly replaced RO water in the RO water chamber 42 to the diluting chambers 43 and 44 and the mixing chamber 46 to wash the chambers, and thereafter discards the RO water to the waste section. Finally, the controller 49 performs the normal reagent preparation operation (steps S3 through S5 of FIG. 14), and discards the prepared reagent from the waste section 306. The automatic washing operation is thus completed.

When the automatic washing ends, the process moves to step S18 of FIG. 15, and the controller 49 stores the measurement results (preparation history information) in the memory unit 49f, and the reagent preparation operation subsequently continues.

When the apparatus stoppage frequency P reaches [2] in step S27 (P is greater than [1]), however, the process moves to step S31. Note that since the value of the apparatus stoppage frequency P is reset to [0] in step S8, for the apparatus stoppage frequency P to reach [2] after the first apparatus stoppage, the measurement result is limited three consecutive "unsuitable" determinations or one "very unsuitable" determination without the measurement result being within the range A1. That is, when the reagent preparation unit 4a is stopped two times consecutively without normally preparing reagent, the process moves to step S31.

In step S31, the controller 49 displays the error message D33 (error display D3a; refer to FIG. 11) on the display/operating unit 48 to warn of an unrecoverable error. The controller 49 also displays an unrecoverable error message D55 in the error detail screen D5a (refer to FIG. 12).

The controller 49 resets the value of the apparatus stoppage frequency P to [0] in step S32, then stores the determination result in the memory unit 49f in step S33 and stops the process. In this case, since the reagent preparation apparatus 4 is stopped under an error condition, the user has specialist service staff to perform maintenance.

In the present embodiment, the controller 49 discards the reagent prepared by the reagent preparation unit 4a when the measurement result of the conductance sensor 402 does not meet the condition of being within the range A1, and continues the reagent preparation operation of the reagent preparation unit 4a until the "unsuitable" determination frequency N (number of reagent discards) reaches three times because the measurement result is not within the range A1, and stops the operation of the reagent preparation unit 4a when the "unsuitable" determination frequency N (number of reagent discards) reaches three times because the measurement result is not within the range A1. Since the reagent preparation continues as the reagent is discarded until the "unsuitable" determination frequency reaches three times, transient failures can be eliminated during the three reagent preparations. Therefore, reduction in the operating efficiency of the reagent preparation unit 4a is avoided because the number of times the reagent preparation unit 4a is stopped can be reduced compared to when the reagent preparation unit 4a is stopped for every "unsuitable" determination. On the other hand, since the reagent preparation unit 4a is stopped after the "unsuitable" determination frequency B reaches three times, the reagent preparation apparatus 4 can be stopped and failure corrected when a persistent failure occurs. Therefore, it is possible to prevent an increase in the amount of wasted reagent caused by continuing reagent preparation when a persistent failure (apparatus breakdown) occurs. According to the reagent preparation apparatus 4 of the present embodiment described above, the amount of wasted reagent is reduced while also avoiding a reduction in the operational efficiency of the apparatus when both transient failures and persistent failures occur.

In this embodiment, the controller 49 is configured to stop the operation of the reagent preparation unit 4a when an "unsuitable" determination is made three consecutive times as the reagent preparation unit 4a continues the reagent preparation operation. According to this structure, since there is a high possibility of a persistent failure (apparatus breakdown) when the "unsuitable" frequency reaches three consecutive times, the reagent preparation unit 4a is reliably stopped when a persistent failure occurs while effectively avoiding stopping the reagent preparation unit 4a when a transient failure occurs.

In the present embodiment, the controller 49 reduces the number of determinations that stop the operation of the reagent preparation unit 4a when the measurement result of the conductance sensor 402 is within the range A3. This construction rapidly stops the reagent preparation when an anomaly occurs in the reagent quality, for example, when urgency is required.

In the present embodiment, when the measurement result of the conductance sensor 402 is within the range A4 and the number of "caution" determinations M reaches five times, the controller 49 displays a warning message D61 (warning display D6; refer to FIG. 13) on the display/operating unit 48 to warn of a high possibility future breakdown of the reagent preparation unit 4a. Thus, the user can initial maintenance of the reagent preparation apparatus 4 before a breakdown. Since the warning message D61 is not displayed if the measurement result of the conductance sensor 402 is within the range A4 only one time, displaying the warning message D61 for a transient failure is largely avoided.

In the present embodiment, when the "unsuitable" determination frequency N reaches three times, the controller 49 stops the operation of the reagent preparation unit 4a and executes an automatic washing operation for the reagent preparation unit 4a as a recovery operation based on the user instruction from the OK button D52 (refer to FIG. 10). According to this construction, a recovery operation can be readily performed when the number of "unsuitable" determinations N reaches three times and the operation of the reagent preparation unit 4a has stopped.

In the present embodiment, when the operation of the reagent preparation unit 4a is stopped two consecutive times in conjunction with the "unsuitable" determination ("very unsuitable" determination), the controller 49 displays an error message D33 (refer to FIG. 11) which warns of the high possibility of breakdown of the reagent preparation unit 4a, and error message D55 (refer to FIG. 12) on the display/operating unit 48. According to this construction, the user easily visually confirms the possibility of breakdown of the reagent preparation unit 4a via the error messages D33 and D55 displayed on the display/operating unit 48.

In the present embodiment, the controller 49 is configured to store the result of the suitable/unsuitable determination in the memory unit 49f for each reagent prepared by the reagent preparation unit 4a. According to this construction, useful information pertaining to performing maintenance operations is obtained because the user knows the history of reagent preparation apparatus 4 failures by the controller 49 storing the suitable/unsuitable determination results.

In the present embodiment, the reagent preparation apparatus 4 is provided with a supply chamber 47 for retaining reagent supplied from the reagent preparation unit 4a to the measuring unit 2; the reagent preparation unit 4a is provided with a waste section 306 for discarding a prepared reagent before the prepared reagent is supplied to the supply chamber 47. According to this construction, the reagent already retained in the supply chamber 47 is not discarded since the reagent determined to be "unsuitable" by the controller 49 is discarded before being delivered to the supply chamber 47. Hence, the amount of wasted reagent determined to be "unsuitable" is reduced compared to when reagent that has been determined to be "unsuitable by the controller 49 is discarded into the supply chamber 47.

Note that the embodiment of the present disclosure is an example in all aspects and not to be considered limiting in any way. The scope of the present invention is expressed by the scope of the claims and not by the description of the embodiment, and includes all meanings and equivalences and modifications pertaining thereunto.

For example, although a sample processing apparatus for blood analysis is described as an example of the sample processing apparatus in the above embodiment, the present invention is not limited to this application. The present invention also may be applied to urine analyzers for analyzing urine samples rather than blood samples. The present invention is applicable insofar as the sample processing apparatus is capable of preparing a reagent for use in a sample measurement.

Although the embodiment is described by way of example in which a reagent is prepared by diluting a high concentration liquid reagent using RO water, the present invention is not limited to this arrangement. The present invention, for example, also may be configured to prepare a reagent by dissolving a powder reagent in a liquid. Rather than diluting a high concentration reagent with RO water, a reagent to be used for sample processing also may be prepared by mixing and reacting a plurality of reagents.

Although the above embodiment is described by way of example in which suitable/unsuitable determination results are classified into the four types of "suitable" determination, "cautionary" determination, "unsuitable" determination, and "very unsuitable" determination, the present invention is not limited to this arrangement. In the present invention, the suitable/unsuitable determination also may be classified in two types of "suitable" determination and "unsuitable" determination. That is, the reagent suitability determination may be based on whether the reagent meets the condition of range A1. Moreover, the reagent suitability determination may be based on three types of "suitable" determination, "unsuitable" determination, and "very unsuitable" determination. The reagent suitability also may be based on five types of determination.

Although the above embodiment is described by way of example in which the suitable/unsuitable determination is made based on electric conductance as a reagent property, the present invention is not limited to this arrangement. In the present invention, the suitable/unsuitable determination is made based on a reagent property other than electric conductance, for example, a pH value.

Although the reagent preparation apparatus is provided with a supply chamber for retaining reagent (reagent determined to be suitable or cautionary) to be delivered to the measuring unit in the above embodiment, the present invention is not limited to this arrangement. In the present invention, the reagent preparation apparatus need not be provided with a supply chamber inasmuch as a reagent prepared by the reagent preparation apparatus may be supplied to the measuring unit without being retained. Further, a reagent supply tank may be provided separately from the reagent preparation apparatus so as to move a prepared reagent from the reagent preparation apparatus to the reagent supply tank.

Although the above embodiment is described by way of example in which the operation of the reagent preparation unit is stopped when the "unsuitable" determination occurs three consecutive times, the present invention is not limited to this arrangement. In the present invention, the operation of the reagent preparation unit also may be stopped when the "unsuitable" determination occurs nonconsecutively a predetermined number of times (the cumulative number of "unsuitable" determinations reaches a predetermined number). For example, the operation of the reagent preparation unit may be stopped when the cumulative number of "unsuitable" determinations reaches a predetermined number (for example, three times) during a predetermined number (for example, ten times) of the reagent preparation operations after an "unsuitable" determination has occurred once.

Although the above embodiment is described by way of example in which the operation of the reagent preparation unit is stopped when the "unsuitable" determination occurs three consecutive times or when a "very unsuitable" determination occurs one time, the present invention is not limited to this arrangement. In the present invention, the number of "unsuitable" determinations required to stop the operation of the reagent preparation unit also may be two times, or four or more times. Similarly, the number of "very unsuitable" determinations needed to stop the operation of the reagent preparation unit may be two or more times. The number of "unsuitable" determinations required to stop the operation of the reagent preparation unit also may be two or more times. In this case, the number of "very unsuitable" determinations may be reduced to fewer than the number of "unsuitable" determinations.

Although an unrecoverable failure message is displayed when the variable P, which represents the number of stoppages of the preparation operation, becomes [2] in the present embodiment, the unrecoverable error message also may be displayed when the variable P becomes [1].

Although in the present embodiment the a "caution" message is displayed if the variable M, which represents the number of "caution" determinations, reaches five, and a "caution" message is displayed each time the variable M reaches 5 because the variable M is reset to 0 after reaching 5, it is to be noted that the present invention is not limited to this arrangement. A "caution" message also may be displayed only once by not resetting the variable M to 0 after the variable M has reached 5. In this case, annoying the user can be avoided by preventing the "caution" message from being displayed numerous times.

Although in the above embodiment a persistent failure is detected when an "unsuitable" determination that the conductance does not match range A1 occurs a predetermined number of consecutive times, this detection need not necessarily use range A1 as the basis of the "unsuitable" determination. A persistent failure also may be detected by changing the range of electric conductance used as a basis of each "unsuitable" determination, for example, determining whether conductance is within range A1 the first time, and determining whether the conductance is within a range different from range A1 the second time.

Although in the above embodiment whether the reagent flowing through the flow pass 305 is "suitable" for sample processing is determined each time reagent is prepared by the reagent preparation unit, that is, each time the reagent is started moving from the mixing chamber 46 to the supply chamber 47, the present invention is not limited to this arrangement. Whether the reagent flowing through the flow pass 305 is "suitable" for sample processing also may be determined each time the reagent is moved from the mixing chamber 46 a plurality of times. In this case, it is preferable that a reagent retaining chamber is further provided between the mixing chamber 46 and the supply chamber 47 to temporarily retain the reagent moved from the mixing chamber 46 in the reagent retaining chamber before reaching the supply chamber 47, and to allow discarding of the reagent within the reagent retaining chamber when there is a possibility that reagent of uncertain quality has been mixed in the reagent retaining chamber. Hence, reagent unsuitable for sample analysis can be prevented from being delivered to the supply chamber 47 even when the quality of the reagent is determined a plurality of times previously.

Although the above embodiment is described by way of example in which the reagent preparation apparatus is provided separately from the measuring unit, the present invention is not limited to this arrangement inasmuch as the reagent preparation apparatus also may be provided within the measuring apparatus to function as a reagent preparation device. The present invention is also applicable to measuring devices (apparatus) provided with a reagent preparation device, for example, cytometers, immunoassay devices, slide preparation apparatuses and the like.

Although the above embodiment is described by way of example in which an error display D3 (refer to FIG. 8) and D3a (refer to FIG. 11), error detail screen D5 (refer to FIG. 10) and D5a (refer to FIG. 12), warning display D6 (refer to FIG. 13) and the like are displayed on the display/operating unit, the present invention is not limited to this arrangement. In the present invention, these may need not be displayed on the display/operating unit.

Although the above embodiment is described by way of example in which preparation history information (i.e., date and time of reagent preparation, reagent measured temperature, reagent measurement result (conductance), and suitable/unsuitable determination result) is stored in a memory unit, the present invention is not limited to this arrangement. In the present invention, the preparation history information need not be stored in a memory unit. Alternatively, only the suitable/unsuitable determination result may be stored in the memory unit. Moreover, only the "unsuitable" determination and "very unsuitable" determination results may be stored in the memory unit.

Although the operation of the controller of the above embodiment is described using a flow-driven flow chart of sequential processes along a process flow, the present invention is not limited to this arrangement. In the present invention, the operation of the controller may also be performed by an event-driven process for executing processes as individual events. In this case, all processes may be event-driven or a combination of event-driven and flow-driven.

What is claimed is:

1. A reagent preparation apparatus configured to prepare a reagent and supply the prepared regent to a measurement section that uses the prepared reagent to analyze a specimen, comprising:
   a supply chamber in which the prepared reagent is storable for stable supply of the reagent to the measurement section;
   a mixing chamber in which a high concentration reagent and water are mixable to prepare the reagent;
   a reagent supply path provided between the mixing chamber and the supply chamber to supply the prepared reagent from the mixing chamber to the supply chamber via the reagent supply path;
   a pump operable to flow the prepared reagent in the reagent supply path;
   a supply valve set operable to communicate the mixing chamber with the supply chamber via the reagent supply path to supply the prepared reagent from the mixing chamber to the supply chamber via the reagent supply path;
   a reagent drain path provided between the mixing chamber and the supply chamber to discard the reagent supplied through the reagent supply path from the mixing chamber before the reagent reaches the supply chamber;
   a drain valve set operable to communicate the reagent drain path with the reagent supply path to discard the reagent supplied through the reagent supply path from the mixing chamber before the reagent reaches the supply chamber;

a quality measuring sensor provided in the reagent supply path upstream of the reagent drain path, the quality measurement sensor being configured to detect a property of the prepared reagent, which is selected from the properties of the prepared reagent consisting of an electric conductance of the prepared reagent and a PH value thereof, to measure a quality of the prepared reagent when the reagent flowing through the reagent supply path from the mixing chamber passes the quality measuring sensor;

a controller programmed to operate, based on the measured quality of the prepared reagent, the supply valve set and the drain valve set to either supply the prepared reagent to the supply chamber from the mixing chamber via the reagent supply path or discard the prepared reagent through the reagent drain path; and a memory operable to store a failure count that counts consecutive determinations that the measure quality of the prepared reagent fails to meet a first quality level, the controller further programmed to:

(a) read the measured quality of the prepared reagent from the quality measuring sensor when the prepared reagent from the mixing chamber passes the quality measuring sensor;

(b) apply a first threshold value representative of the first quality level against the measured quality read from the quality measuring sensor to determine whether the measured quality satisfies the first quality level or fails to meet the first quality level;

(c) responsive to a determination by the controller that the measured quality satisfies the first quality level, operate the supply valve set to supply the prepared reagent to the supply chamber from the mixing chamber via the reagent supply path and reset the failure count to zero;

(d) responsive to a determination by the controller that the measured quality fails to meet the first quality level, operate the drain valve set to discard the prepared reagent from the mixing chamber through the reagent drain path before the prepared reagent reaches the supply chamber and increment the failure count; and (e) repeat operations (a)-(d), and responsive to the failure count incremented above a predetermined failure count, stop operation of the reagent preparation apparatus.

2. The reagent preparation apparatus of claim 1, wherein the controller is further programmed to read the measured quality from the quality measuring sensor each time the prepared reagent flowing through the reagent supply path from the mixing chamber passes the quality measuring sensor.

3. The reagent preparation apparatus of claim 1, wherein the failure count is indicative of consecutive determinations by the controller that the measured quality fails to meet the first quality level.

4. The reagent preparation apparatus of claim 1, wherein the controller is further programmed to:
apply a second threshold value against the measured quality to determine whether the measured quality satisfies or fails to meet a second quality level, wherein the second quality level is representative of a quality level lower than the first quality level; and
responsive to a determination by the controller that the measure quality fails to meet the second quality level, stop operation of the reagent preparation apparatus.

5. The reagent preparation apparatus of claim 4, wherein the controller is further programmed to, responsive to a determination by the controller that the measured quality fails to meet the first quality level, apply the second threshold value against the measured quality to determine whether the measured quality satisfies or fails to meet the second quality level.

6. The reagent preparation apparatus of claim 1, wherein the controller is further programmed to:
receive an instruction to initiate a recovery operation after the controller stops operation of the reagent preparation apparatus in operation (e); and
in response to a reception of the instruction to initiate the recovery operation, execute the recovery operation to restart the reagent preparation apparatus, wherein the recovery operation includes discarding any reagent left in the mixing chamber and thereafter washing the mixing chamber.

7. The reagent preparation apparatus of claim 1, further comprising a display unit, wherein
the memory is operable to store a stop count that counts a number of consecutive stops performed in operation (e),
operation (c) comprises resetting the stop count, and
operation (e) comprises incrementing the stop count,
the controller is further programmed to
(f) repeat operations (a)-(e), and responsive to the stop count incremented above a second predetermined stop count, display, on the display unit, a warning that an unrecoverable error has occurred in the reagent preparation apparatus.

8. The reagent preparation apparatus of claim 7, wherein the memory is operable to store a caution count, and
the controller is further programmed to:
(g) apply a third threshold value against the measured quality to determine whether the measured quality falls between the first quality level and a third quality level, wherein the third quality level is representative of a quality level higher than the first quality level, and thus the measured quality that falls between the first and third quality levels satisfies the first quality level;
(h) responsive to a determination by the controller that the measure quality is higher than the third quality level, reset the caution count to zero;
(i) responsive to a determination by the controller that the measure quality falls between the first and third quality levels, increment the caution count; and
(j) repeat operations (a) and (g)-(i), and responsive to the caution counter incremented above a third predetermined caution count, display, on the display unit, an warning that there is a high possibility that operation of the reagent preparation apparatus will fail.

9. The reagent preparation apparatus of claim 1, wherein the controller is configured to store, in the memory, a history of determinations made by the controller on a respective flows of the prepared reagent that the measured quality satisfies or fails to meet the first quality level.

10. The reagent preparation apparatus of claim 1, further comprising a reagent retaining chamber in which the prepared reagent supplied from the mixing chamber is temporarily storable before the prepared reagent is supplied to the supply chamber, the reagent retaining chamber being located in the reagent supply path and communicable with the mixing chamber and the supply chamber, wherein the controller is further programmed to:
responsive to a determination by the controller in operation (c) that the measured quality satisfies the first quality level, operate the supply valve set to supply the prepared reagent stored in the reagent retaining chamber to the supply chamber via the reagent supply path; and responsive to a determination by the controller in operation (d) that the measured quality fails to meet the first quality level, operate the drain valve set to discard the prepared reagent stored in the reagent retaining chamber through the reagent drain path.

11. The reagent preparation apparatus of claim 10, wherein the quality measuring sensor is located upstream of the reagent retaining chamber along the reagent supply path.

12. The reagent preparation apparatus of claim 1, wherein the quality measuring sensor is configured to measure an electric conductance of the prepared reagent.

13. The reagent preparation apparatus of claim 1, wherein the reagent is prepared in the mixing chamber by mixing a plurality of types of liquids.

14. The reagent preparation apparatus of claim 1, wherein the specimen is blood, and the reagent is a diluting liquid for diluting the blood.

* * * * *